United States Patent [19]

Hoie

[11] Patent Number: 4,516,726

[45] Date of Patent: May 14, 1985

[54] MIXING AND SPRAYING APPARATUS FOR LIQUIDS, OPTIONALLY FOR POWDER AND LIQUID

[76] Inventor: Karl H. Høie, Hemings vei 4, Oslo 3, Norway

[21] Appl. No.: 487,191

[22] Filed: Apr. 19, 1983

[30] Foreign Application Priority Data

Feb. 24, 1983 [NO] Norway ................................. 830657

[51] Int. Cl.³ .............................................. B05B 7/26
[52] U.S. Cl. .................................... 239/317; 239/142; 239/310
[58] Field of Search ................ 239/310, 317, 318, 142, 239/365–367, 698; 137/268, 802, 888, 896; 366/154, 165, 349

[56] References Cited

U.S. PATENT DOCUMENTS

| | | | |
|---|---|---|---|
| 811,749 | 2/1906 | Somers | 239/317 |
| 3,498,540 | 3/1970 | Adams | 239/698 |
| 3,943,960 | 3/1976 | Syrenne | 239/317 |

*Primary Examiner*—Andres Kashnikow
*Assistant Examiner*—James R. Moon, Jr.
*Attorney, Agent, or Firm*—Browdy and Neimark

[57] ABSTRACT

A mixing and spraying apparatus for liquids, optionally for powder and liquid, comprising two branch lines on a conduit conveying water under pressure. One branch line passes tangentially through the tank wall into the mixing tank and causes the water in the mixing tank to rotate in a vortex to mix with the added liquid or powder that is introduced into the top opening of the tank in batches or continuously by means of suitable equipment for this purpose. The other branch line passes radially into the tank through the lower wall portion of the tank and terminates in a nozzle, which together with an open end of an outlet conduit forms an injection pump for conveying the admixed components from the mixing tank to a spray hose and nozzle that are connected to the outlet conduit. By means of respective spigots, the feed conduit and outlet conduit can be opened and closed and the branch lines can be regulated in relation to each other for obtaining optimum vortex formation in the mixing tank and for adjusting the desired capacity of the injection pump, which guides the admixed components from the mixing tank through the outlet conduit to the hose and nozzle. Said lines and spigots can be built as a separate unit for insertion into an open-top mixing tank.

14 Claims, 2 Drawing Figures

MIXING AND SPRAYING APPARATUS FOR LIQUIDS, OPTIONALLY FOR POWDER AND LIQUID

BACKGROUND OF THE INVENTION

The present invention relates to a mixing and spraying apparatus for liquids, optionally for powder and liquid, of the type recited in the preamble of the appurtenant independent claim 1.

A number of different types of mixing apparatus are known for mixing two or more different liquids and for mixing liquids and solids in the form of powders and/or particles, which may either be dissolved in the liquid or held in suspension until the mixture is to be used or conveyed to the user.

SUMMARY OF THE INVENTION

The objective of the present invention is to provide a mixing and spraying apparatus wherein a liquid, preferably in the form of cold or hot water, is introduced into a mixing tank and additional liquid or powder is added and mixed with the first liquid, after which the admixed components, under pressure, are transferred from the tank to the user via an outlet conduit which may be connected to a hose with a nozzle for spraying the admixed components, or the mixture may be conducted to an overhead spray unit or to showers in a sanitation system, or to another container for storage.

This is obtained in accordance with the invention by means of a mixing and spraying apparatus whose characterizing features are recited in the characterizing clause of the appurtenant independent claim 1 and in the succeeding dependent claims.

The mixing and spraying apparatus of the invention is a simple and robust apparatus which is simple to produce and easy to regulate. The apparatus is also easy to put into operation, provided that cold/hot water under pressure is available at the intended site of use, the additional liquid or powder being added via the opening at the top of the mixing tank.

The mixing and spraying apparatus can be produced as a complete unit in which all of the components are connected to the mixing tank, or the hoses and control valves/spigots which constitute a main part of the mixing and spraying apparatus may be constructed as a separate unit for insertion into a mixing tank at the top opening of the tank. The mixing and spraying apparatus of the invention is primarily intended for use in connection with operations in the field, such as for mixing and spraying components for spraying plants, trees, the ground, houses, vehicles and other machinery as well as human beings, to purify or detoxify non-desirable substances disseminated in some way in the atmosphere or on personnel and objects. Applications also include disinfectant spraying for combating various types of infectious substances.

The invention will be discussed in greater detail in the following with reference to the accompanying drawings, which schematically illustrate two embodiments of the invention.

DESCRIPTION OF THE PREFERRED EMBODIMENTS

Figure 1:
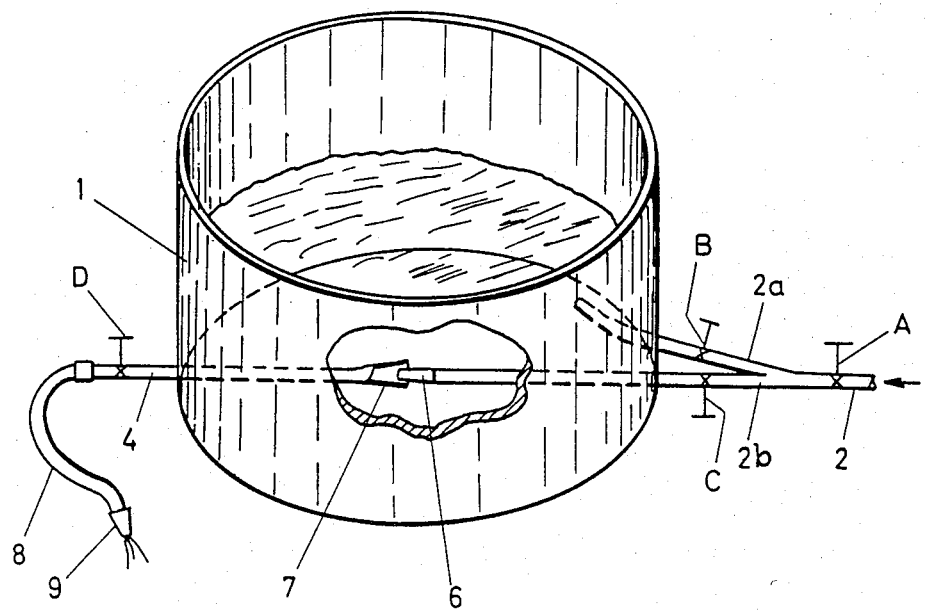
FIG. 1, in perspective, shows the mixing and spraying apparatus with the mixing tank as a complete unit.

FIG. 1 shows a mixing tank 1 with a feed line 2 for introducing liquid under pressure, preferably water, with branch lines 2a, 2b entering the mixing tank 1 through the lower wall section thereof. The branch line 2a discharges tangentially in the mixing tank, which preferably is round, and the branch line 2b passes radially into the mixing tank 1—near the bottom of the tank—and discharges via a nozzle 6 into an open, outwardly diverging end 7 of an outlet conduit 4, said conduit end 7 preferably being disposed centrally in the tank 1 vis-a-vis the nozzle 6. The outlet conduit 4 is this in alignment with the feed line 2, and extends radially through the tank 1 to exit through the tank wall at the lower section of the tank. The nozzle 6 and said open end 7 of the outlet conduit together form an injection pump. The feed line 2 is provided with a control valve or spigot A upstream of the branch lines 2a, 2b, each of which has a respective control valve/spigot B,C, and the outlet conduit 4 is also provided with a control valve/spigot D. The outlet conduit 4 may be connected to a hose 8 with a nozzle 9, or to a shower head in a sanitation system, or to a collection tank (not illustrated).

To operate the mixing and spraying apparatus, the feed line 2 is connected to water under pressure. The spigot A is opened, the spigot B is opened for filling the mixing tank 1 to the desired level, and then the spigot D in the outlet conduit 4 is opened and the spigot C in the branch line 2b is regulated so that with the aid of the above-mentioned injection pump, a desired quantity of liquid under pressure is led out of the tank via the outlet conduit 4, discharging through the optional associated hose 8 and nozzle 9. The liquid or powder which is to be dissolved in the water may be added to the tank in batches or continuously, by means of suitable equipment for this purpose which will not be described in further detail in this specification. The tangentially-directed nozzle of the branch line 2a causes a vortex which effectively mixes the added liquid or powder with the water in the mixing tank 1. The mixture is then drawn into the injection pump 6, 7 and discharged together with the water flowing in through the branch line 2b through the outlet conduit 4, as explained above.

After the mixing tank 1 has been filled to the desired level, the spigots B, C are regulated to maintain the desired water level in the tank during the subsequent mixing and spraying of the admixed components. To shut off the mixing and spraying apparatus, the spigot A for the feed line 2 and optionally the spigot D for the outlet conduit 4 are turned off, while the spigots B and C in the branch lines 2a, 2b can remain in the positions previously set, in readiness for the next use of the apparatus.

Figure 2:
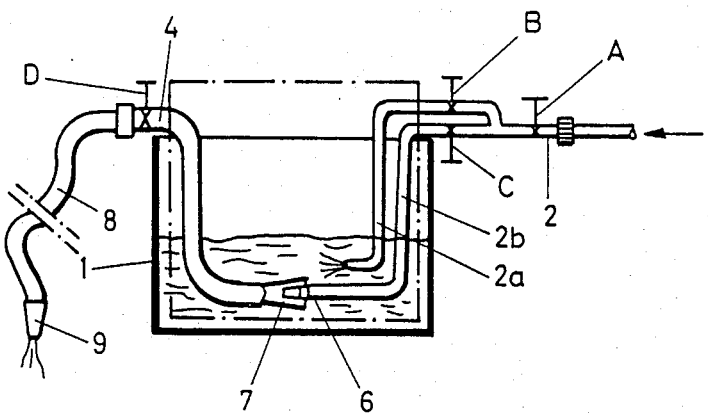
FIG. 2 shows the mixing and spraying part of the apparatus as a separate unit for lowering into a mixing tank.

In the embodiment illustrated in FIG. 2, said lines 2, 2a,2b,4 with the spigots A,B,C,D are assembled into a unit 10, indicated with broken lines in the drawing, for insertion into an open tank 1, which may either be brought along separately or which is already found at the intended site of use.

To obtain favorable currents of flow in the water in the mixing tank 1, the outlet nozzle for the branch line 2a may be adjustable to permit it to be set at a desired direction in the mixing tank 1. Alternately, in addition to or instead of adjusting the discharge direction of the branch line 2a, baffles can be provided in the tank, in a manner known per se, to cause the water to flow in the desired vortex for mixing the components in the desired manner.

Having described my invention, I claim:

1. A mixing and spraying apparatus for liquids, optionally for powder and liquid in admixture, including a preferably round mixing tank with a feed line for liquid under pressure and an outlet conduit with a control valve/spigot, wherein additional liquid or powder is introduced into the tank via the top opening of the tank, the liquid feed line being divided into a first, and a second, branch, the second branch discharging via a nozzle into an open end of the outlet conduit within the tank at the lower section of the tank thereby forming an injection pump for carrying and conveying the admixed media through the outlet conduit to an optional connected hose with a spray nozzle or some other spray means, the mixing and spraying apparatus comprising:
    said mixing tank being at atmospheric pressure,
    said first branch discharging into the lower section of the mixing tank for introducing liquid into the tank and for forming a vortex to facilitate admixture of said liquid with a powder or optionally with another liquid which may be introduced from the top of the tank, and
    each branch including a control valve or spigot.

2. A mixing and spraying apparatus according to claim 1, wherein both branches enter the mixing tank through the lower wall portion thereof and the outlet conduit is located vis-a-vis the second branch and exits through the lower wall portion of the tank.

3. A mixing and spraying apparatus according to claim 1, wherein the discharge end of the first branch discharges tangentially into the mixing tank.

4. A mixing and spraying apparatus according to claim 3, wherein the direction in which the discharge end of the first branch discharges may be regulated.

5. A mixing and spraying apparatus according to claim 1, wherein said liquid feed line and associated spigots are arranged as a separate unit for placement in an open-top mixing tank.

6. An apparatus for mixing a first liquid with a second liquid or a powder and spraying the admixture, comprising:
    a tank into which said second liquid or said powder may be introduced,
    conduit means for feeding said first liquid under pressure, said conduit means including first and second branches, and
    an outlet conduit for said admixture having one end disposed within said tank and a second end leading from said tank to a spraying device,
    said first branch discharging tangentially into said tank and causing a vortex flow within said tank,
    said second branch having one end disposed within said vortex flow in said tank and discharging said first liquid into said outlet conduit one end, said outlet conduit one end and said second branch one end being so close in proximity as to define means for inducing flow of said admixture in said tank into said outlet conduit one end.

7. The apparatus of claim 6 wherein said second branch one end is disposed within said outlet conduit one end.

8. The apparatus of claim 6 and further including means for regulating flow of said first liquid to said tank.

9. The apparatus of claim 8, wherein said regulating means comprise valves in said first and second branches.

10. The apparatus of claim 9, wherein said regulating means further comprises a valve in said conduit means.

11. The apparatus of claim 6, and further including means for introducing said first fluid to said conduit means continuously.

12. The apparatus of claim 6, and further including means for introducing said first fluid to said conduit means in batches.

13. The apparatus of claim 6, wherein said first branch discharges into said tank from a nozzle, said nozzle being adjustable so that the direction of discharge of said first liquid into said tank may be adjusted.

14. The apparatus of claim 13, wherein said nozzle is disposed within said tank.

* * * * *